United States Patent [19]

Holcombe

[11] 4,176,053
[45] Nov. 27, 1979

[54] N-PARAFFIN - ISOPARAFFIN SEPARATION PROCESS

[75] Inventor: Thomas C. Holcombe, Scarsdale, N.Y.

[73] Assignee: Union Carbide Corporation, New York, N.Y.

[21] Appl. No.: 892,334

[22] Filed: Mar. 31, 1978

[51] Int. Cl.$^2$ .............................................. C10G 25/04
[52] U.S. Cl. ............................... 208/310 Z; 585/822; 585/825
[58] Field of Search .............. 208/310 Z; 260/676 MS

[56] References Cited

U.S. PATENT DOCUMENTS

| | | | |
|---|---|---|---|
| 3,373,103 | 3/1968 | Cooper et al. | 208/310 Z |
| 3,393,097 | 7/1968 | Senn | 208/310 Z |
| 3,700,589 | 10/1972 | Symoniak et al. | 208/310 Z |

Primary Examiner—Herbert Levine
Attorney, Agent, or Firm—Richard G. Miller

[57] ABSTRACT

Normal paraffins are isolated from a feedstock mixture of normal and non-normal paraffins in the vapor phase at superatmospheric pressure using an adsorption system comprising at least four fixed adsorption beds containing a 5 Angstrom molecular sieve adsorbent, each of which cyclically undergoes the stages of (a) adsorption-fill, (b) adsorption, (c) void space purging, and (d) purge desorption. The improvement of the present process comprises recycling in the vapor phase in combination with feedstock the mixture of isoparaffins and normal paraffins purged from one bed of the system during stage (c) to another bed of the system undergoing stage (b). In conventional practice the void space contained hydrocarbons purged from each bed during stage (c) was cooled, separated from the purging gas, pumped to a holding tank in the liquid phase and thereafter reheated to form the vapor phase before being admixed with fresh feedstock for further treatment.

5 Claims, 1 Drawing Figure

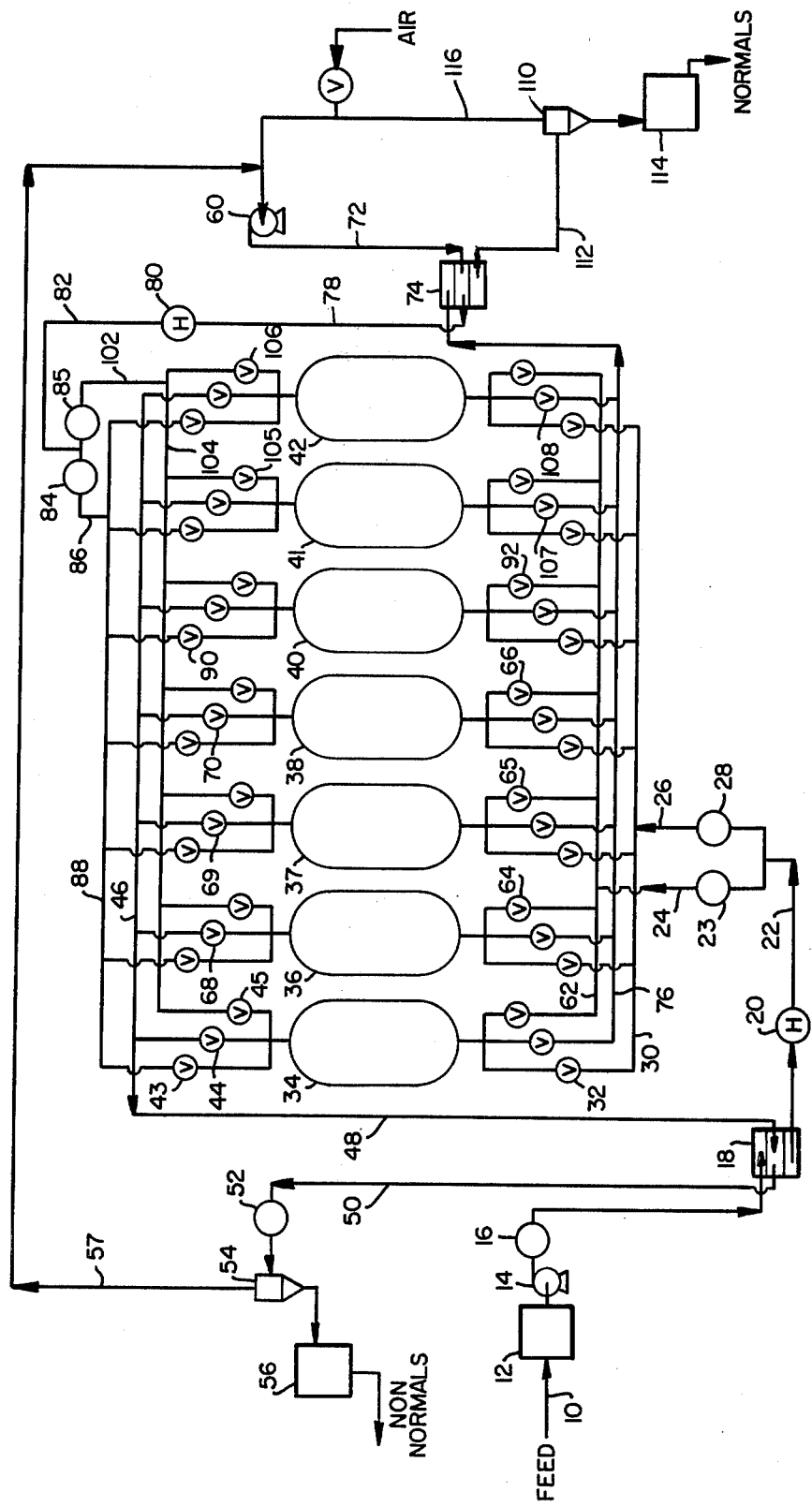

N-PARAFFIN - ISOPARAFFIN SEPARATION PROCESS

The present invention relates in general to the separation of mixtures of normal and non-normal paraffins, and more particularly to the separation of normal paraffins from mixed paraffin feedstock by selective adsorption on crystalline zeolitic molecular sieves.

The separation of mixtures of chemical compounds into two or more fractions by selective adsorption based on molecular size is a conventional procedure which takes advantage of the uniform diameters of pores of a given zeolitic molecular sieve adsorbent. The separation of normal paraffins from isoparaffins has been found to be particularly adapted to this technique and a number of processes have been proposed for this purpose. Most of them have been based on contacting the mixed hydrocarbon feed in the vapor phase with a 5 Angstrom molecular sieve to adsorb the straight chain hydrocarbon compounds followed by desorption of the straight chain compounds at a lower pressure or higher temperature usually with the aid of a purge gas. Some have been done with little or no change in temperature of pressure by employing a purge which is sufficiently strongly adsorbed to exert a displacing action on the adsorbed straight chain compounds. One process of particular interest operates under essentially isobaric and isothermal conditions even though desorption is accomplished using a non-sorbable purge gas instead of a strongly sorbable purge material. That process is defined in detail in U.S. Pat. No. 3,700,589, issued Oct. 24, 1972, the disclosure of which is incorporated herein in its entirety by reference. The process of the present invention is an improvement on that process.

In accordance with the present process for separating normal paraffins from admixture with non-normal paraffins by passing a feedstock mixture of same in the vapor state and at superatmospheric pressure periodically in sequence through each of at least four fixed beds of a system containing a zeolitic molecular sieve adsorbent having effective pore diameters of substantially 5 Angstroms, each of said beds cyclically undergoing the stages of:

(a) adsorption-fill, wherein the vapor in the bed void space consists principally of a non-sorbable purge gas and the incoming feedstock forces the said non-sorbable purge gas from the bed void space out of the bed without substantial intermixing thereof with non-adsorbed feedstock fraction;

(b) adsorption, wherein the feedstock is cocurrently passed through said bed and the normal constituents of the feedstock are selectively adsorbed into the internal cavities of the crystalline zeolitic adsorbent and the nonadsorbed constituents of the feedstock are removed from the bed as an effluent having a greatly reduced content of non-feedstock constituents;

(c) void space purging, wherein the bed loaded with normals adsorbate to the extent that the stoichiometric point of the mass transfer zone thereof has passed between 85 and 97 percent of the length of the bed and containing in the bed void space a mixture of normals and non-normals in essentially feedstock proportions, is purged countercurrently, with respect to the direction of adsorption stage (b), by passing through the bed a stream of a non-sorbable purge gas in sufficient quantity to remove said void space feedstock vapors but not more than that which produces about 50 mole percent, preferably not more than 40 mole percent, of adsorbed feedstock normals in the bed effluent; and (d) purge desorption, wherein the selectively adsorbed feedstock normals are recovered as a product stream by passing a non-sorbable purge gas countercurrently with respect to adsorption stage (b) through the bed until the major proportion of adsorbed normals has been desorbed and the bed void space vapors consist principally of non-sorbable purge gas;

the improvement which comprises recycling directly in the vapor phase in combination with feedstock the mixture of normals and non-normals purged from each bed of the system during stage (c) to another bed of the system undergoing stage (b) adsorption.

In conventional practice the effluents from the beds during void space purging, stage (c), have been cooled to condense the higher boiling paraffin constituents, flashed to remove and recover any non-sorbable purge material, pumped in the liquid phase to a point in the system where combination with fresh feedstock is feasible, and reheated to the gas phase for reprocessing. By virtue of the present improvement, not only are all of these operations avoided, but also there is provided the advantage of reducing the non-normals/normals molar ratio in the stage (b) feedstock, thereby improving the purity of the stage (d) effluent normals.

The molecular sieve adsorbent employed in the present process can be any of the naturally occurring or synthetically produced three-dimensional crystalline zeolitic aluminosilicates from which the water of hydration can be removed without collapse of the crystal lattice and which will selectively, on the basis of molecular size, adsorb normal paraffins from the mixture thereof with branched chain and/or cyclic paraffins which comprises the feed stream. Since normal paraffins have a minimum cross-sectional diameter of about 5 Angstroms, molecular sieves having pore diameters of about 5 Angstroms are preferred for the practice of the present invention. Especially suitable are the cation forms of zeolite A which have pore diameters of about 5 Angstroms. Zeolite A is well known in the art as a synthesized zeolite having a very large adsorption capacity and, depending on the cation species present, exhibit apparent pore diameters ranging from about 3 to about 5 Angstroms. As prepared in the sodium cation form, zeolite A has pore diameters of about 4 Angstroms. When 25 percent, preferably at least 40 percent, of the sodium cations are exchanged by calcium and/or magnesium cations, the effective pore diameter increases to about 5 Angstroms. Zeolite A as used herein in the Specification and claims is intended to denote the zeolite described and defined in U.S. Pat. No. 2,882,243. Other zeolitic molecular sieves which, in appropriate cation forms, have pore diameters of about 5 Angstroms and which, although having less adsorption capacity than zeolite A, are suitably employed include zeolite T, U.S. Pat. No. 2,950,952 and the minerals chabazite and erionite.

The hydrocarbon streams treated in accordance with the present invention consist essentially of mixtures of branched chain paraffins and normal paraffins boiling in the gasoline and kerosene ranges. Such mixtures occur as petroleum naphthas, both light and heavy, natural gasolines and natural gas condensates, but can be the products of processed outside the petroleum production and refining industry. In general, the hydrocarbons of these streams contain from about 4 to about 13 carbon atoms and preferably are substantially free of olefinically and acetylenically unsaturated species. It is also advantageous that sulfur compound impurities, if present, be present in a concentration less than about 400 parts per million, and the water impurity levels are below saturation. Although the process is operable regardless of the relative molar proportions of normals and non-normals present in the feed, the greatest benefit is afforded when the process is operated as one of bulk separation wherein both non-normals and normal paraffins each constitute at least 10 mole percent of the feedstock.

The entire process is operated at a substantially uniform temperature selected from the range of about 350° F. to 750° F. At temperatures below about 350° F., the efficiency of the non-sorbable purge gas is decreased to the point where undesirably large quantities are required adequately to purge the normals from the bed. Above about 750° F., the rate of coke deposition increases rapidly and the need for more frequent oxidative regnerations of the adsorbent arises. It is to be understood that the denomination of the present process as being "isothermal" is done so for the reason that the temperature of the feed and purge gas stream are essentially the same, i.e., within about 30° F. when entering the bed. In this, as in any adsorption-desorption cycle, it is possible for thermal gradients to develop in the bed due to heats of adsorption and desorption.

The pressure range suitable for the present process is from about 50 psia to about 400 psia. In general, the preferred pressure is dependent on the particular feedstock involved, with the higher pressures being used for the more volatile feedstocks to enhance the separation obtained and to facilitate the condensation of the product effluents. It is important that none of the feedstock components condense in the void space of the bed since such liquid phase material cannot be removed by the limited quantity of nonsorbable purge gas allotted for this purpose.

Accordingly, the pressure is to be maintained at less than 80 percent of the critical pressure of the highest boiling key component of the feed or less than about 60 percent of the dew point pressure of the feed at the process temperature, whichever is the lower value. Similarly, as in the case of the term "isothermal" supra, the process is termed "isobaric" because the pressure of the adsorber feed and purge gas streams are within conventional limits the same at their respective influent ends of the bed. The term "isobaric" is thus used in its accepted sense in the art to indicate that the present process does not utilize a pressure swing type of desorption. By the term "key component" used herein in conjunction with the delineation of pressure requirements is meant any paraffinic constituent of the feed mixture which is present in significant amount. As is well understood in the art, what constitutes a significant quantity of a particular component of a mixture depends somewhat on the other components present and the nature of the treatment the feed is undergoing. Generally, however in the present process, a key component will be present in an amount of about 10 mole percent or greater.

When the pressure conditions are dictated by the dew point criterion, the dew point of the hydrocarbon mixture involved can be determined by the procedure set forth in "Process Heat Transfer," Kern, Donal Q., McGraw-Hill Book Company, New York, N.Y. (U.S.A.), at pages 319 to 325 inclusive. Other procedures are well known in the art to make these calculations. Routine experimentation can, of course, be resorted to, instead of calculating the dew point.

The non-sorbable purge gas used to flush the bed void space vapors and carry from the bed desorbed normal paraffins in this process is any permanent gas or mixture of such gases which have molecular dimensions sufficiently small to enter the intracrystalline cavities of the molecular sieve, but are not themselves strongly enough adsorbed to displace the normal hydrocarbons adsorbed thereon to any significant degree. Nitrogen, hydrogen, helium and methane are such materials and are preferred in the practice of this invention. Other permanent gases are known in the art, but lack of commercial availability at reasonable cost renders them impractical although operable.

Bed void space for purposes of this invention is intended to means any space in the bed not occupied by solid material except the intracrystalline cavities of the zeolite crystals. The pores within any binder material which may be used to form agglomerates of the zeolite crystals is considered to be bed void space.

As stated hereinbefore, the adsorption stroke wherein the normal paraffins are selectively adsorbed on the bed is continued for a period such that the stoichiometric point of the normal hydrocarbons mass transfer zone has moved through between 85 and 97 percent of the bed length. The term mass transfer zone as used herein has the same meaning as is generally accepted in the art, i.e., it denotes that section of the adsorbent bed in which the adsorbate loading of the adsorbent bed and the concentration of the adsorbate fraction in the fluid stream are both increasing with time. The "stoichiometric point" lies within the mass transfer zone and is that point at which the expended capacity of the leading section of the mass transfer zone is equal to the unexpended capacity of the transfer zone.

In order to optimize the four stage cycle of the present process and to give a substantially constant flow of both normal and non-normal hydrocarbon product streams, it is preferred to use at least four adsorption beds of essentially equal capacity in an integrated time-controlled sequence. This system provides optimum conditions for heat exchange and purge gas recovery, as well as favorable mass transfer and pressure drop characteristics during the adsorption stage (b). All process valves can be automatically controlled from a timer control system. For purposes of illustrating the invention, the following description is provided in conjunction with the drawing which is a flow diagram of such a four stage cycle process using a seven bed adsorbent system. For purposes of the exemplification, it is presumed that the system has already attained a steady state. The temperature of all primary adsorption beds and all feed streams to and effluents therefrom is 700° F. The beds are under a pressure of about 250 psia. The composition of the primary feedstock is shown in tabular form below:

TABLE I

| Saturated Hydrocarbon | Non-normals, wt. -% of Component in Feed | Wt. -% Normals in Feedstock |
|---|---|---|
| $C_3$ | | Trace |
| $C_4$ | 0.60 | 1.60 |
| $C_5$ | 33.37 | 12.52 |
| $C_6$ | 44.66 | 5.92 |
| $C_7$ | 1.33 | Trace |
| $C_8^+$ | Trace | Trace |

With reference to the drawing, the feed stream is fed through line 10 to accumulator tank 12 from which it is drawn by pump 14 through a feed rate controller 16 and thereafter heat exchanger 18 where it is heated to about 450°–500° F. by heat exchange with effluent from an adsorption bed undergoing second stage adsorption. The partially heated feed stream is raised to full 700° F. operating conditions in a gas fired heater 20. The flow rate of the feed stream from heater 20 into line 22 is 336,578 pounds per hour and has a normal paraffin content of about 20.0 wt.-%. The stream from line 22 is directed partially to line 24 by way of pressure controller 23 (the use of which will be described later) and partially to line 26 by means of flow rate controller 28 in line 26. Through line 26 the minor portion of the feed from line 22, namely 99,026 pounds per hour, is directed through manifold 30 and valve 32 to adsorption bed 34. Each of the seven adsorption beds in the system, namely beds 34, 36, 37, 38, 40, 41 and 42 contain 93,000 pounds of calcium zeolite A in the form of 1/16 inch cylindrical pellets. Each bed is 17.5 feet long and 12.5 feet in diameter. Bed 34, at the time that feed passing through valve 32 enters, contains residual hydrogen purge gas from the preceding desorption stroke. The rate of flow of the feed through line 26, manifold 30 and valve 32 is controlled such that bed 34 is flushed of residual hydrogen uniformly over a period of about one minute i.e., the effluent from bed 34 exits at a rate of about 3,845 pounds per hour. During this first stage of the adsorption stroke in bed 34, the hydrogen effluent passes from the bed through valve 45 into manifold 104. During the one minute period when the hydrogen was being flushed from bed 34, feed passes from valve 23 through line 24, through manifold 62, and valves 64, 65 and 66 to beds 36, 37 and 38 respectively at the rate of 79,184 pounds per hour. The normal paraffins in the feed are adsorbed by each of beds 36, 37, 38 and the non-adsorbed non-normals emerge from the beds through valves 68, 69, 70 respectively and are fed to manifold 46. The non-normals flow through line 48, heat exchanger 18, line 50, water cooler 52, separator 54 and the condensed product is accumulated in accumulator 56. The residual hydrogen purge gas in the non-normals effluent leaves separator 54 through line 57, to purge recycle compressor 60. During the one minute period when the residual hydrogen is being flushed from bed 34, i.e., stage (a), bed 40 is undergoing the first stage of purging with hydrogen wherein the hydrocarbons in the bed void space are being flushed from the bed, i.e., stage (c). During the same one minute interval, beds 41 and 42 are undergoing the second stage of desorption, i.e., stage (d), in which the normal hydrocarbons are desorbed from the molecular sieve adsorbent using hydrogen and removed from the bed. From compressor 60, the hydrogen gas stream is passed through line 72 and through heat exchanger 74 wherein it is heated to about 550°–600° F. by heat from hot desorbed normals from any of the adsorption beds flowing through manifold 76. From the heat exchanger 74 the hydrogen gas stream passes through line 78 to gas fired heater 80 where it is heated to 700° F. and hence through line 82. By means of flow controllers 84 and 85 the gas flow from line 82 is divided into two streams, the lesser stream being passed at the rate of 7,709 pounds per hour through line 86, manifold 88, and valve 90 countercurrently (with respect to the previous adsorption stroke) through bed 40. The low controlled flow rate employed for the one minute first stage desorption is for the purpose of flushing non-adsorbed hydrocarbon from the bed voids without causing excessive desorption of the normals from the adsorbent. The effluent from bed 40, consisting of 124,693 pounds per hour hydrocarbon and 2,038 pounds per hour hydrogen passes through valve 92 and into manifold 62. The effluent from the first stage of desorption containing the void space loading from the previous adsorption stroke plus any desorbed normals is recycled directly to the feed used during the second stage of adsorption without intermediate cooling, phase separation and reheating. In fact, valve 92 is used as the second stage adsorption feed valve when bed 40 is on that step in the cycle. The major portion of the hydrogen stream from line 82, namely 37,659 pounds per hour is passed through control valve 85, line 102, to manifold 104 where it is mixed with the previously mentioned first stage adsorption effluent from valve 45 and thence equally through valves 105 and 106 through beds 41 and 42. During this period, selectively adsorbed normal paraffins are desorbed from the zeolitic molecular sieve and flushed from the bed. The effluent from beds 41 and 42 consisting of 85,543 pounds per hour normal paraffins and 20,654 pounds per hour hydrogen are fed through valves 107 and 108 to manifold 76 and thereafter through heat exchanger 74. The cooled normal paraffins and hydrogen leaving heat exchanger 74 are fed to separator 110 through line 112 wherein the normals are fed to normals accumulator 114 and the hydrogen recycled to purge recycle compressor 60 through line 116.

The foregoing description is for a single one minute period of seven minute cycle of the system. For the next one minute period, appropriate valves are operated so that bed 34 begins a second stage adsorption stroke beds 37 and 38 remain on second stage adsorption, bed 36 begins a first stage desorption, bed 40 enters a second stage desorption, bed 41 remains on desorption and bed 42 begins a first stage adsorption stroke. Similarly a new cycle begins after each one minute period and at the end of a seven minute period, the beds have all gone through all stages of adsorption and desorption. The following chart indicates the functioning of each of the seven beds for each one minute period. In the chart, A-1 denotes the stage (a) adsorption in which a bed is flushed of residual hydrogen using a feedstock stream at low feed rates. A-2 denotes a conventional adsorption stroke, i.e., the stage (b) adsorption herein, in which the rate of feed of the hydrocarbon mixture is commensurate with efficient use of the bed. D-1 denotes the stage (c) desorption in which purge gas is used in an amount sufficient to remove hydrocarbon vapor from the bed void spaces, and D-2 denotes stage (d), i.e., hydrogen purge using flow rates sufficient to desorb normals from the bed.

|           | TIME SEQUENCE | | | | | | |
|-----------|-----|-----|-----|-----|-----|-----|-----|
| TIME, min. | 0 | 1 | 2 | 3 | 4 | 5 | 6 |
| Bed 34 | A-1 | A-2 | A-2 | A-2 | D-1 | D-2 | D-2 |
| Bed 36 | A-2 | D-1 | D-2 | D-2 | A-1 | A-2 | A-2 |
| Bed 37 | A-2 | A-2 | D-1 | D-2 | D-2 | A-1 | A-2 |
| Bed 38 | A-2 | A-2 | A-2 | D-1 | D-2 | D-2 | A-1 |
| Bed 40 | D-1 | D-2 | D-2 | A-1 | A-2 | A-2 | A-2 |
| Bed 41 | D-2 | D-2 | A-1 | A-2 | A-2 | A-2 | D-1 |
| Bed 42 | D-2 | A-1 | A-2 | A-2 | A-2 | D-1 | D-2 |

The purpose of valve 23 in the A-1 feed line 24 is best shown by the following example. Assume a feed pressure in line 22 of 250 psia and also assume for purposes of this example that flow control valves 28, 84 and 85 and all line have negligible pressure drop. Then A-1 feed lines 26 and 30 are at 250 psia. A-1 effluent line 104 reflecting the pressure drop through the adsorber vessel is at 249 psia. This then must be the pressure of lines 102, 82, 86 and the D-1 feed line 88. The D-1 effluent line 62 reflecting the pressure drop through the adsorber vessel is at 246 psia. Since line 62 and line 24 are also the A-2 feed lines, their pressure is about 246 psia. In this example, therefore, line 24 must be controlled by valve 23 to 4 psi lower than line 22 to ensure the mixing of D-1 effluent and the A-2 feed.

As a bed is cycled at the 700° F. operating temperature, a carbonaceous deposit gradually accumulates. This deposit reduces the capacity of the adsorbent, which results in a breakthrough of normal paraffins into the isomer product stream and decreased normal paraffin recovery. The rate at which this deposit accumulates depends on factors such as temperature, feed impurities, feed properties, cycle time, and residual paraffin loadings. This type of adsorbent deactivation is temporary as that original bed capacity can be restored by burning off this deposit under controlled conditions.

Oxidative regeneration is a blocked operation with burnoff of the five adsorbent beds in sequence, and is required to maintain the working capacity of the molecular sieve. The basis for this procedure is a three-day shutdown consisting of the following stages:

| Stage: | Time, hrs. |
|---|---|
| (1) System preparation for regeneration | 2 |
| (2) Oxidative regeneration | 68 |
| (3) System preparation for adsorption step | 2 |
| Total time | 72 |

When the beds have been cycled to the point that oxidative regeneration is required, the normal process cycle is shut down, and the beds undergo an additional long desorption purge to remove as much of the residual normal paraffins as possible. Countercurrent circulation of nitrogen is established by means of the purge gas compressor 60 at 100 psia and 750° F. The circulation of the hot nitrogen has two purposes, namely to sweep the purge gas from the bed if it is combustible (i.e., fuel gas, hydrogen, etc.), and to raise the temperature of the bed to above the coke ignition point prior to introduction of oxygen into the system. The effluent gas from the beds manifold 76 is cooled to condense the hydrocarbons and water that are desorbed. When the bed is up to temperature, air is introduced into the circulating stream at a rate such that the oxygen content of the gas entering the bed is between 0 and 1 percent by volume. The oxygen in the gas combusts with coke in the top of the bed. The heat released from combustion is carried out of the burning zone as a preheat front traveling ahead of the burning front. This preheat front raises the bed temperature to about 950° F. This temperature is controlled by regulating the amount of oxygen in the entering gas. Internal pellet temperatures in excess of 1300° F. will permanently destroy the molecular sieve crystal so the gas phase temperature is held to a maximum of 1000° F. As the burning front passes through the bed, the temperature will drop back to the gas inlet temperature of 750° F. Since the coke deposit contains hydrogen, water is formed during combustion in addition to carbon oxides. This water must be removed from the system because the molecular sieve is permanently damaged by repeated exposure to water at high temperatures. A refrigeration unit is used to remove most of the water, thereby minimizing this damage.

After the regeneration is complete, the beds are cooled down to the process operating temperature and purged of any remaining oxygen by circulating nitrogen. The beds are now ready to go on stream in the normal process cycle.

What is claimed is:

1. In the process for separating normal paraffins from admixture with non-normal paraffins which comprises passing a feedstock mixture of same in the vapor state and at superatmospheric pressure periodically in sequence through each of at least four fixed beds of a system containing a zeolitic molecular sieve adsorbent having effective pore diameters of substantially 5 Angstroms, each of said beds cyclically undergoing the stages of:

(a) adsorption-fill, wherein the vapor in the bed void space consists principally of a non-sorbable purge gas and the incoming feedstock forces the said non-sorbable purge gas from the bed void space out of the bed without substantial intermixing thereof with non-adsorbed feedstock fraction;

(b) adsorption, wherein the feedstock is cocurrently passed through said bed and the normal constituents of the feedstock are selectively adsorbed into the internal cavities of the crystalline zeolitic adsorbent and the non-adsorbed constituents of the feedstock are removed from the bed as an effluent reduced in content of non-feedstock constituents;

(c) void space purging, wherein the bed loaded with normals adsorbate to the extent that the stoichiometric point of the mass transfer zone thereof has passed between 85 and 97 percent of the length of the bed and containing in the bed void space a mixture of normals and non-normals in essentially feedstock proportions, is purged countercurrently, with respect to the direction of adsorption stage (b), by passing through the bed a stream of a non-sorbable purge gas in sufficient quantity to remove said void space feedstock vapors but not more than that which produces about 50 mole percent of adsorbed feedstock normals in the bed effluent; and (d) purge desorption, wherein the selectively adsorbed feedstock normals are recovered as a product stream by passing a non-sorbable purge gas countercurrently with respect to adsorption stage (b) through the bed until the major proportion of adsorbed normals has been desorbed and the bed void space vapors consist principally of non-sorbable purge gas;

the improvement which comprises recycling directly in the vapor phase in combination with feedstock the mixture of normals and non-normals purged from each bed of the system during stage (c) to another bed of the system undergoing stage (b) adsorption.

2. Process according to claim 1 where the temperature of the adsorption beds is within the range of from about 350° F. to 700° F. and the pressure is from about 50 psia to 400 psia.

3. Process according to claim 2 wherein the non-sorbable purge gas is hydrogen.

4. Process according to claim 1 wherein the zeolitic molecular sieve is calcium zeolite A.

5. Process according to claim 2 wherein the hydrocarbons comprising the mixture of normal paraffins and non-normal paraffins contain from 4 to 13 carbon atoms and the mixture is substantially free of olefinically and acetylenically unsaturated hydrocarbons.

* * * * *